United States Patent [19]
Felder et al.

[11] Patent Number: 5,639,675
[45] Date of Patent: Jun. 17, 1997

[54] METHOD OF IDENTIFYING A NONPARAFFINOPHILIC MICROORGANISM USING VARIOUS MILIEUS AND AN ASSOCIATED APPARATUS

[75] Inventors: Mitchell S. Felder, Hermitage; Robert-A. Ollar, Milford, both of Pa.

[73] Assignee: Infectech, Inc., Sharon, Pa.

[21] Appl. No.: 555,742

[22] Filed: Nov. 9, 1995

[51] Int. Cl.$^6$ .............................. C12Q 1/02; C12Q 1/04; C12Q 1/24; G01N 33/48

[52] U.S. Cl. ........................... 435/29; 435/34; 435/4; 435/30; 435/36; 435/42; 436/63; 436/74

[58] Field of Search .................... 435/29, 34, 4, 435/30, 36, 42; 436/63, 74

[56] References Cited

U.S. PATENT DOCUMENTS

| | | | |
|---|---|---|---|
| 3,826,717 | 7/1974 | Gilbert et al. | 435/34 |
| 4,683,195 | 7/1987 | Mullis et al. | 435/6 |
| 4,683,201 | 7/1987 | Hamill et al. | 435/6 |
| 4,683,202 | 7/1987 | Mullis | 435/6 |
| 4,692,407 | 9/1987 | Jordan et al. | 435/29 |
| 4,782,025 | 11/1988 | Inoue et al. | 435/29 |
| 5,153,119 | 10/1992 | Ollar | 435/34 |
| 5,316,918 | 5/1994 | Ollar | 435/34 |

OTHER PUBLICATIONS

Wallace et al., *Chest*, 93(5) 926–932 (1988).
Wolinsky, *American Review of Respiratory Disease*, vol. 119:107–159 (1979).
Horsburgh, Jr. et al., *Medicine*, vol. 64, No. 1: 36–48 (1983).
Horsburgh, Jr. et al., *American Review of Respiratory Disease*, 139: 4–7 (1989).
C.M. Reichert et al., *AIDS: Etiology, Diagnosis Treatment and Prevention*, p. 134, Lippencott (1985).
C.C. Hawkins et al., *Annals of Internal Medicine*, 105: pp. 184–188 (1986).
J. Hoy et al. *The Journal of Infectious Diseases*, 161: 801–805 (1990).
Fuhs, G.W., *Arch Mikrobiol*, 39:374–422 (1961).
Mishra, S.K. et al., *Mycopathologia et Mycologia Applicata*, vol. 51 (2–3): 147–157 (1973).
Ollar, *Zbl. Bakt. Hyg. I.Abt. Orig. A 234:* 81–90 (1976).
Kemper et al., *American Society for Microbiology*, 297 (Abstract) (1990).
Klatt et al., *Human Pathology*, vol. 18, No. 7: 709–714 (1987).
Bermudez et al., *The Journal of Infectious Diseases*, 165: 75–79 (1992).
Murphy et al., *American Society for Microbiology*, 277 (1983).
P. Ma et al., *AIDS and Infections of Homosexual Men*, 233–234 (1989).
Havlik Jr. et al., *The Journal of Infectious Diseases*, 165: 577–580 (1992).
Inderlied et al., *AIDS Clinical Review*, 165–191 (1990).
Gonzalez et al., *Diagn. Microbiol. Infect. Dis.*, 8: 69–77 (1987).
Ollar et al., *Tubercle*, 71, pp. 23–28 (1990).
Kemper et al., *Annals of Internal Medicine*, 116: 466–472 (1992).
Heifets et al., *Antimicrobial Agents and Chemotherapy*, 1298–1301 (1989).
Hurley et al., *Journal of Clinical Microbiology*, pp. 1582–1587 (1989).
Kirihara et al., *Journal of Clinical Microbiology*, pp. 841–845 (1985).

*Primary Examiner*—John Kight
*Assistant Examiner*—Louise Leary
*Attorney, Agent, or Firm*—David V. Radack; Eckert Seamans Cherin & Mellott

[57] ABSTRACT

A method of determining the presence or absence of a nonparaffinophilic microorganism in a specimen taken from a patient. The method includes providing a receptacle containing an aqueous solution and adjusting the solution to mimic the in vivo clinical conditions of the patient. The method further includes inoculating the solution with the specimen and then placing in the receptacle a slide coated with a carbon source to bait the nonparaffinophilic microorganism. The slide is then analyzed after exposure to the specimen to determine the presence or absence of the nonparaffinophilic microorganism. An associated apparatus is also disclosed.

14 Claims, 1 Drawing Sheet

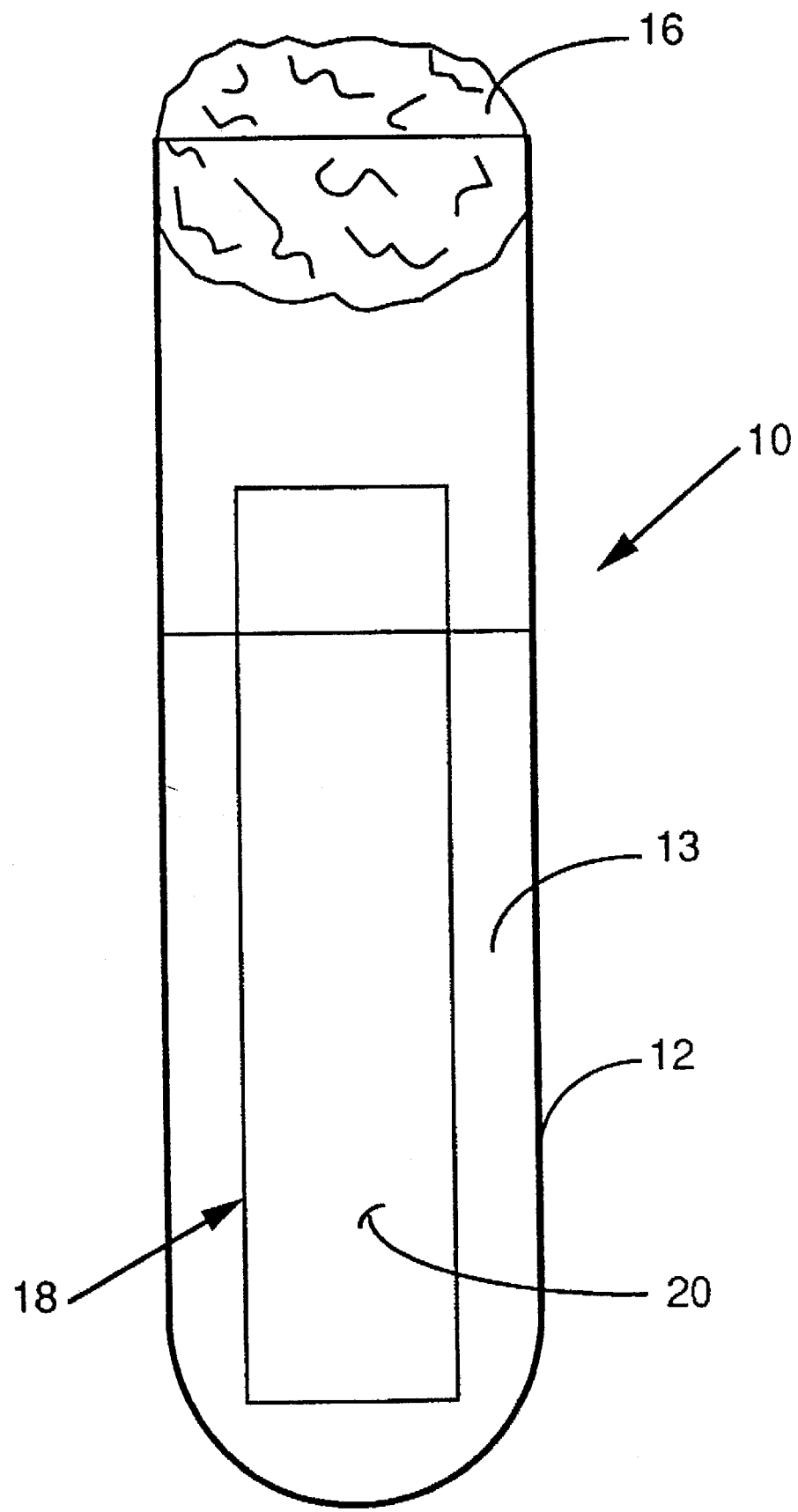

METHOD OF IDENTIFYING A NONPARAFFINOPHILIC MICROORGANISM USING VARIOUS MILIEUS AND AN ASSOCIATED APPARATUS

BACKGROUND OF THE INVENTION

This invention relates to a method of identifying a nonparaffinophilic microorganism using various milieus and an associated apparatus.

Identification of nonparaffinophilic microorganisms in a clinical specimen is an important part of medical treatment of patients. Often times, educated guesses as to the nature of the microorganism involved are made. It thus would be beneficial to improve the process of identifying these microorganisms with a simple, effective method and apparatus.

U.S. Pat. Nos. 5,153,119 and 5,316,918 disclose methods and apparatus for identifying and testing the antibiotic sensitivity of *Mycobacterium avium-intracellulare* ("MAI"), a paraffinophilic microorganism. The inventor named on those patents is Robert-A. Ollar, one of the co-inventors of the invention disclosed herein. This method involves providing a receptacle containing an aqueous solution and inoculating into the solution a specimen. After this, a paraffin coated slide is placed into the receptacle. The slide is then observed for the presence or absence of growth of MAI.

Despite the efficient, effective and economical method disclosed in Dr. Ollar's patents, there still remains a need for a simple and effective method to determine the presence or absence of a nonparaffinophilic microorganism.

SUMMARY OF THE INVENTION

The invention has met or surpassed the above-mentioned need as well as others. The method of determining the presence of a nonparaffinophilic microorganism in a specimen taken from a patient includes providing a receptacle containing an aqueous solution and adjusting the solution to mimic the in vivo clinical conditions of the patient. The method further includes inoculating the solution with the specimen and then placing in the receptacle a slide coated with a carbon source. The slide is then analyzed after exposure to the specimen to determine the presence or absence of the nonparaffinophilic microorganism.

An apparatus to facilitate determination of the presence of a nonparaffinophilic microorganism in a specimen taken from a patient is also provided. The apparatus comprises a receptacle for holding an aqueous solution and a slide coated with a carbon source adapted to be placed in the receptacle. The apparatus further comprises means for adjusting the aqueous solution to mimic the in vivo clinical conditions of the patient.

BRIEF DESCRIPTION OF THE DRAWING

A full understanding of the invention can be gained from the following detailed description of the invention when read in conjunction with the accompanying lone drawing which shows a front elevational view of a test tube holding a slide coated with a carbon source in an aqueous solution inoculated with a specimen.

DETAILED DESCRIPTION

As used herein, the term "nonparaffinophilic microorganism" means any microorganism sustained by a carbon source other than paraffin. Examples of such nonparaffinophilic microorganisms include, but are not limited to, the following: *Helicobacter pylori*; *Hemophilus influenzae*; *Salmonella typhimurium*; *Mycobacterium tuberculosis*; *Mycobacterium paratuberculosis*; *Mycobacterium leprae*; Staphylococcus; Streptococcus; *E. Coli*; Listeria; Brucellae; Humemophilus; Treponema; Pneumococcus; Clostridium; Cryptococcus; Coccidioides; and Histoplasma. Also, as used herein, the term "patient" refers to a member of the animal kingdom, including human beings, whose body specimen is being processed by the method and apparatus of the invention.

The method and apparatus of the invention provide an efficient, effective and economical way of identifying a nonparaffinophilic microorganism. Referring now to the lone Figure, an embodiment of a nonparaffinophilic microorganism identification apparatus 10 is shown. The apparatus 10 includes a standard test tube 12 which contains an aqueous solution 13 and a cotton plug 16 to seal the test tube 12. According to the invention, a specimen to be tested for the presence or absence of a nonparaffinophilic microorganism is inoculated into the aqueous solution 13. A slide 18 having a coating comprising or containing a carbon source 20 is then placed into the test tube 12. The carbon source 20 is a growth media for growing the nonparaffinophilic microorganism. It will be appreciated that the aqueous solution 13 should not contain any carbon source, as it is desired to provide a sole carbon source 20 on the slide 18 in order to effectively grow the nonparaffinophilic microorganism to be identified on the slide 18 and not in the aqueous solution 13. Growth on the slide 18, which can either be seen or unseen by the unaided human eye, can be analyzed to determine the presence or absence of a nonparaffinophilic microorganism. Preferably, a minimum of twenty-four (24) hours incubation time is necessary for growth to occur. In order to analyze the slide 18 after the incubation period, the slide 18 can be scraped using a flame sterilized spatula and subcultured on an agar-like tryptic soy agar (TSA). If the scrapings include growth, the growth on the TSA can be analyzed using classical microbiological procedures or can be analyzed using a DNA extraction process involving either organic solvent extraction or column chromatographic extraction.

The specimen to be inoculated into the test tube 12 can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques in known standard ways.

The carbon source 20 on the slide 18 can include a gelatinous matrix containing a carbon source. A carbon source can be one or more of those selected from the group consisting of glucose, fructose, glycenol, mannitol, asparagine and casein, among others. Another embodiment can include providing a slide and coating the slide with an adhesive and securing a plurality of gel beads to the adhesive. The carbon source can then be either ionically or affinity bound to the gel beads.

The slide 18 with the gelatinous matrix containing a carbon source can be prepared by the following method. A receptacle, such as a laboratory beaker, is first filled with 100 ml of distilled water. Into the beaker is placed two (2) grams of agar (the gelatinous matrix) and three (3) grams of a carbon source (such as glucose). This mixture is then boiled and steam sterilized and the molten gelatinous matrix with a carbon source is poured into a petri dish, which is sitting on a hot plate. In this way the gelatinous matrix/carbon source remains molten. After this, a sterile slide 18 is dropped into the molten gelatinous matrix/carbon source and becomes coated therewith. The now coated slide is removed from the petri dish and allowed to stand for a minute or two in order to solidify the coating 20 thereon. The slide with the coating of a gelatinous matrix containing a carbon source is then ready to be placed in the test tube 12 containing the aqueous solution 13 and the specimen.

An alternative method of preparing the slide involves first coating the slide with an adhesive, such as collodion and then applying a plurality of gel beads (commercially available from Pharmacia of Parsippany, New Jersey) to the adhesive. The gel beads are approximately one micron in diameter. The slide containing the coating of gel beads is now immersed in a buffering agent containing the carbon source (such as glucose) to attach the carbon source to the gel beads either ionically or affinity-wise.

Nonparaffinophilic microorganisms that can be identified using the method of the invention include any microorganism sustained by a carbon source other than paraffin. Nonparaffinophilic microorganisms include, but are not limited to, Helicobacter pylori; Hemophilus influenzae; Salmonella typhimurium; Mycobacterium tuberculosis; Mycobacterium paratuberculosis; Mycobacterium leprae; Staphylococcus; Streptococcus; E. Coli; Listeria; Brucellae; Humemophilus; Treponema; Pneumococcus; Clostridium; Cryptococcus; Coccidioides; and Histoplasma.

In accordance with the invention, the aqueous solution 13 can be adjusted to mimic the in vivo "clinical conditions" of the patient before placing the slide 18 in the receptacle 12 and before inoculating the specimen into the aqueous solution 13. By "clinical conditions" it is meant at least one of the following: (i) the pH of the in vivo milieu of the patient where the nonparaffinophilic microorganism can be found and (ii) the electrolyte levels of a patient's blood where nonparaffinophilic microorganisms can be found. Adjusting the aqueous solution can be effected by numerous different methods. Adjusting the pH of the aqueous solution can be accomplished by adding hydrochloric acid (HCl) to obtain a more acidic solution or by adding sodium hydroxide (NaOH) or potassium hydroxide (KOH) in order to obtain a more basic solution. Electrolytes such as one or more selected from the group consisting of sodium, potassium, chloride, magnesium, phosphate and calcium, can be added to the solution in desired quantities in order to mimic the electrolytes in the blood of a patient from which a blood sample which may contain the nonparaffinophilic microorganism is obtained.

EXAMPLE 1

A patient comes to an emergency room at a hospital complaining of severe abdominal pain. A gastroenterologist uses a gastrointestinal scope to obtain a specimen of the patient's stomach fluid. The scope indicates that the pH in the patient's stomach is 3.5. In the meantime, a lab technician using the apparatus of the Figure adjusts the pH of the aqueous solution 13 by adding HCl thereto so that the aqueous solution 13 has a pH of 3.5. Thus, the pH in the patient's stomach is mimicked by the pH of the aqueous solution in the apparatus shown in the Figure. After this, the specimen of stomach fluid taken by the gastroenterologist from the patient is inoculated into the receptacle 12 holding a slide coated with a carbon source 18. After about eight days a growth appears on the slide 18. The growth is then analyzed by conventional methods to determine the presence or absence of a nonparaffinophilic microorganism, such as for example Helicobacter pylori.

EXAMPLE 2

A patient comes to an emergency room complaining of high fever and apparently has pneumonia. As is standard in almost every emergency room, a chemical screen ("CSS") is performed on a blood specimen obtained from the patient. The CSS lists the electrolyte content of the patient's blood. The electrolyte content is communicated to a lab technician who in turn adjusts the aqueous solution 13 in the receptacle 12 holding the slide coated with a carbon source 18. For example, the CSS reveals that the patient has a sodium level of 120. The lab technician adjusts the sodium level of the aqueous solution (for example, distilled water) by adding sodium thereto in order to mimic the 120 level of sodium found in the patient's blood. The blood specimen is then inoculated into the adjusted aqueous solution. After about two days a growth appears. The growth is analyzed and is found to be a nonparaffinophilic microorganism.

It will be appreciated that a method for identifying a nonparaffinophilic microorganism has been disclosed in which the aqueous solution in which the paraffin coated slide and the nonparaffinophilic microorganism are placed is adjusted to mimic the in vivo clinical conditions of a patient from whom the specimen containing the nonparaffinophilic microorganism to be identified is obtained. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source; and analyzing said slide after exposure to said specimen to determine the presence or absence of said nonparaffinophilic microorganism.

2. The method of claim 1, including employing as said specimen one selected from the group consisting of blood, stomach fluid, urine, cerebral spinal fluid, nasopharyngeal mucosa and saliva.

3. The method of claim 1, including effecting said adjusting of said aqueous solution by altering the pH of said aqueous solution.

4. The method of claim 3, including altering said pH of said aqueous solution by adding chemicals to said aqueous solution.

5. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source;

analyzing said slide after exposure to said specimen to determine the presence or absence of said nonparaffinophilic microorganism;

altering said pH of said aqueous solution by adding chemicals to said aqueous solution; and employing as said chemicals one selected from the group consisting of HCl, KOH and NaOH.

6. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source;

analyzing said slide after exposure to said specimen to determine the presence or absence of said nonparaffinophilic microorganism; and effecting said adjusting of said aqueous solution by adding chemicals to said solution to mimic the electrolyte level in said patient's blood.

7. The method of claim 6, including employing as said chemicals at least one of the group consisting of sodium, potassium, chloride, magnesium, phosphate and calcium.

8. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source;

analyzing said slide after exposure to said specimen to determine the presence or absence of said nonparaffinophilic microorganism; and employing as said slide one coated with a gelatinous matrix containing said carbon source.

9. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source;

analyzing said slide after exposure to said specimen to determine the presence or absence of said nonparaffinophilic microorganism; and providing said slide by first adhering to said slide a plurality of gel beads and then bonding to said gel beads said carbon source.

10. The method of claim 9, wherein said carbon source is ionically bound to said gel beads.

11. The method of claim 9, wherein said carbon source is affinity bound to said gel beads.

12. The method of claim 9, including adhering said gel beads to said slide by means of an adhesive.

13. The method of claim 12, including employing as said adhesive collodion.

14. A method of determining the presence or absence of a nonparaffinophilic microorganism in a specimen taken from a patient, said method comprising:

providing a receptacle containing an aqueous solution;

adjusting said aqueous solution to mimic the in vivo clinical conditions of said patient;

inoculating said solution with said specimen;

placing into said receptacle a slide coated with a carbon source;

analyzing said slide after exposure to said specimen to determine the presence or absence of said nonparaffinophilic microorganism; and employing as said carbon source one or more of the group consisting of glucose, fructose, glycenol, mannitol, asparagine and casein.

* * * * *